United States Patent
Mizuno et al.

(10) Patent No.: US 9,914,838 B2
(45) Date of Patent: Mar. 13, 2018

(54) SURFACE TREATMENT SOLUTIONS FOR GOLD AND GOLD ALLOYS

(71) Applicant: Rohm and Haas Electronic Materials LLC, Marlborough, MA (US)

(72) Inventors: Yoko Mizuno, Shibata (JP); Makoto Kondo, Niigata (JP); Koichi Yomogida, Niigata (JP); Toshiyuki Morinaga, Niigata (JP)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 15/157,453

(22) Filed: May 18, 2016

(65) Prior Publication Data

US 2017/0002211 A1 Jan. 5, 2017

(30) Foreign Application Priority Data

Jun. 30, 2015 (JP) ................. 2015-131719

(51) Int. Cl.

| | | |
|---|---|---|
| B05D 5/12 | (2006.01) | |
| C09D 5/08 | (2006.01) | |
| H05K 1/03 | (2006.01) | |
| H05K 3/00 | (2006.01) | |
| C07D 333/04 | (2006.01) | |
| C25D 3/38 | (2006.01) | |
| C08K 5/3462 | (2006.01) | |
| C07D 233/02 | (2006.01) | |
| C25D 11/24 | (2006.01) | |
| C09D 7/12 | (2006.01) | |
| C09D 179/04 | (2006.01) | |
| C23C 26/00 | (2006.01) | |
| C25D 5/48 | (2006.01) | |
| H01L 21/288 | (2006.01) | |
| C08G 73/06 | (2006.01) | |
| C08G 59/00 | (2006.01) | |
| H05K 1/00 | (2006.01) | |
| C07D 233/00 | (2006.01) | |
| C08K 5/00 | (2006.01) | |
| C08K 3/32 | (2006.01) | |
| C25D 5/12 | (2006.01) | |

(52) U.S. Cl.
CPC ............. *C09D 5/08* (2013.01); *C07D 233/02* (2013.01); *C07D 333/04* (2013.01); *C08G 73/0616* (2013.01); *C08K 5/3462* (2013.01); *C09D 7/1216* (2013.01); *C09D 179/04* (2013.01); *C23C 26/00* (2013.01); *C25D 3/38* (2013.01); *C25D 5/48* (2013.01); *C25D 11/246* (2013.01); *H01L 21/288* (2013.01); *H05K 1/0346* (2013.01); *H05K 3/00* (2013.01); *C07D 233/00* (2013.01); *C08G 59/00* (2013.01); *C08K 3/32* (2013.01); *C08K 5/00* (2013.01); *C08K 2003/324* (2013.01); *C25D 5/12* (2013.01); *H05K 1/00* (2013.01)

(58) Field of Classification Search
CPC .......... H05K 1/00; H05K 1/0346; H05K 3/00; C09D 179/04; C08G 73/0616; C08G 59/00; C08K 3/32; C08K 5/3462; C08K 5/00; C25D 5/48; C25D 11/246; C25D 3/38; C07D 285/088; C07D 233/02; C07D 233/00; C07D 333/04
See application file for complete search history.

(56) References Cited

U.S. PATENT DOCUMENTS

| | | | | |
|---|---|---|---|---|
| 3,616,283 A | * | 10/1971 | Magee | ..... C25D 5/02 101/37 |
| 5,599,630 A | * | 2/1997 | Smith | ..... C08J 7/047 428/301.4 |
| 5,607,570 A | | 3/1997 | Rohbani | |
| 5,658,970 A | * | 8/1997 | Harris | ..... C08G 59/56 204/499 |
| 6,787,606 B1 | * | 9/2004 | Chen | ..... C08L 63/00 359/265 |
| 7,128,822 B2 | | 10/2006 | Wang et al. | |
| 9,212,429 B2 | | 12/2015 | Yomogida et al. | |
| 2003/0100638 A1 | | 5/2003 | Yamamuro et al. | |
| 2006/0162820 A1 | | 7/2006 | Dietsche et al. | |
| 2012/0132533 A1 | * | 5/2012 | Yomogida | ..... C25D 3/62 205/268 |
| 2012/0318676 A1 | | 12/2012 | Najjar et al. | |
| 2013/0048505 A1 | | 2/2013 | Niazimbetova et al. | |

FOREIGN PATENT DOCUMENTS

| | | | |
|---|---|---|---|
| CN | 103510133 A | | 1/2014 |
| JP | 03-199381 | * | 8/1991 |
| JP | 7258894 | | 10/1995 |
| JP | 994598 | | 4/1997 |
| JP | 9170096 | | 6/1997 |

(Continued)

OTHER PUBLICATIONS

JP,03-199381, English Translated, Nakamura Iseo, 1991.*
Search report for corresponding Europe Application No. 16 17 4877 dated Nov. 4, 2016.
Search report for corresponding Taiwan Application No. 105118039 dated Mar. 6, 2017.
Search report for corresponding China Application No. 201610444326.2 dated Sep. 27, 2017.

*Primary Examiner* — David P Turocy
*Assistant Examiner* — Mohammad Mayy
(74) *Attorney, Agent, or Firm* — John J. Piskorski

(57) ABSTRACT

A composition containing a cationic polymer obtained from a reaction product of nitrogen-containing heterocyclic compound and epihalohydrin; and a phosphorus compound. The composition can be used as a surface treatment for gold or gold alloy. The composition can seal pinholes on the surface of the gold or gold alloy.

10 Claims, No Drawings

(56) References Cited

FOREIGN PATENT DOCUMENTS

JP 2003129257 5/2003
JP 200957596 3/2009

* cited by examiner

SURFACE TREATMENT SOLUTIONS FOR GOLD AND GOLD ALLOYS

FIELD OF THE INVENTION

The present invention relates to a surface treatment solution for gold or gold alloys, and more particularly, relates to a sealing agent for the surface of gold or gold alloys.

BACKGROUND OF THE INVENTION

Gold plating has been widely used in recent years in electronic equipment and electronic components, particularly to protect the connection terminal surface of electronic components because the gold has excellent electrical properties, corrosion resistance, and the like. Gold plating is also used as the surface treatment of the electrode terminals of semiconductor elements and as the surface treatment of electronic components such as connectors to connect electronic equipment. The electronic components, such as connectors, are generally made of copper or copper alloys. In order to usually apply gold plating on these electronic components, the nickel plating is applied at first on the copper surface as base plating, followed by gold plating on the nickel plating layer. However, since gold is an expensive noble metal, the thickness of the gold plating film is reduced as much as possible to use a smaller amount of gold and to reduce the manufacturing cost when manufacturing these electronic components.

However, the number of pinholes in the gold plating film increases with decreasing gold plating film thickness. These pinholes cause problems such as corrosion of underlying metal nickel and base metal copper, raise the contact resistance by deposition of the corrosion reaction product on the surface, and the like if water, chlorides, and other such corrosive substances penetrate the pinholes.

Sealing treatment is one of the methods to solve this problem. The sealing treatment is a surface treatment for gold to improve corrosion resistance by covering pinholes by the action of chemicals on the surface of the gold plating film. Japanese laid-open patent publication No. 9-170096 describes a sealing treatment solution containing an inhibitor and a self-emulsifier, and Japanese laid-open patent publication No. 2003-129257 describes a water-based sealing agent containing an inhibitor, a surfactant, and an amine compound. In these documents, benzotriazole and the like are exemplified as inhibitor, and during sealing treatment, DC electrolysis is carried out by using the plating material as anode. However, for the method of performing electrolysis in the sealing treatment, additional equipment is required for sealing treatment. On the other hand, the present inventors conducted studies and found that when an aqueous solution containing benzotriazole as the sealing agent is used and DC electrolysis is not performed, the sealing of the pinholes is not enough, thus corrosion may occur. Therefore, it has been desired to develop a sealing agent highly capable of sealing pinholes with a simple treatment method without performing electrolysis.

SUMMARY OF THE INVENTION

As a result of intensive studies, the present inventors discovered that by using a composition containing a cationic polymer which is a reaction product of a nitrogen-containing heterocyclic compound and epihalohydrin; and a phosphorus compound, it is possible to perform a high sealing treatment without performing electrolysis such as mentioned in prior art documents. Thus, based on these findings, the present invention has been accomplished.

The present invention relates to a composition containing a cationic polymer which is a reaction product of a nitrogen-containing heterocyclic compound and epihalohydrin; and a phosphorus compound. The phosphorous compound is preferred to be at least one compound selected from the group consisting of phosphoric acids, polyphosphoric acids and salts thereof and phosphate esters.

The present invention also relates to a surface treatment agent for gold or gold alloys containing a cationic polymer which is a reaction product of a nitrogen-containing heterocyclic compound and epihalohydrin; and a phosphorus compound. The phosphorous compound is preferred to be at least one compound selected from the group consisting of phosphoric acids, polyphosphoric acids and salts thereof and phosphate esters. The content of the cationic polymer and the phosphorous compound is preferred to be from 0.01 to 70 g/L and 0.01 to 50 g/L, respectively.

The present invention further relates to a surface treatment method for gold or gold alloys comprising a step of contacting the surface of the gold or gold alloys with an aqueous solution containing a cationic polymer which is a reaction product of a nitrogen-containing heterocyclic compound and epihalohydrin; and a phosphorus compound.

Therefore, a primary object of the present invention is to provide a sealing agent for the surface of gold or gold alloys capable of sealing the surface of the gold or gold alloys.

DETAILED DESCRIPTION OF THE INVENTION

As used throughout the specification ° C. is degree Celsius, g/L is grams per liter, ml/L is milliliters per liter, μm is micrometer, m/min is meters per minute, and $A/dm^2$ and ASD are Amperes per square decimeter.

The present invention pertains to a surface treatment agent made of a composition containing a cationic polymer which is a reaction product obtained from a nitrogen-containing heterocyclic compound and epihalohydrin; and a phosphorus compound. Examples of the nitrogen-containing heterocyclic compounds include imidazole and pyridine. Halogens of epihalohydrins include fluoro, chloro, bromo or iodo. Examples of epihalohydrins include epichlorohydrin and epibromohydrin. Examples of the cationic polymer obtained by reacting nitrogen-containing heterocyclic compounds with epihalohydrins include those obtained by dissolving and reacting imidazole and epichlorohydrin at a desired concentration in the same solvent; however, commercially available products may also be used. Examples of commercially available products include RALU®PLATE IME manufactured by Raschig chemicals (product name) (CAS No.: 68797-57-9). The content of the cationic polymer obtained by reacting nitrogen-containing heterocyclic compounds with epihalohydrins in the composition is from 0.01 to 70 g/L, preferably from 1 to 20 g/L.

The composition of the preset invention uses a cationic polymer obtained by reacting nitrogen-containing heterocyclic compounds and epihalohydrins; and a phosphorous compound in a mixture. The phosphorous compounds include phosphoric acids, polyphosphoric acids and salts thereof, and phosphate esters, preferably at least one kind selected from these. Here, the polyphosphoric acid is obtained by dehydration condensation of two or more phosphoric acids. The polyphosphoric acid includes metaphosphoric acid and tri-polyphosphoric acid. The salts of phosphoric acids and polyphosphoric acids refer to inorganic or organic salts of these acids. Examples thereof include sodium, potassium, ammonium, and guanidine salts. Phosphate esters are obtained by substituting a hydrogen atom of at least one hydroxyl group of phosphoric acid by ($C_1$ to $C_6$) alkyl. Examples include phosphoric acid trimethyl, phosphoric acid triethyl, and the like. The content of the phosphorous compound in the composition is from 0.01 to 50 g/L, preferably from 10 to 30 g/L.

The composition of the present invention can also contain a pH adjuster, a wetting agent as optional components. The composition of the present invention also uses water as the solvent; preferably deionized water can be used. The pH of the composition of the present invention is from 6 to 12, preferably from 8 to 12.

The composition of the present invention can be used as a surface treatment agent for gold or gold alloys. More preferably, it is used as a sealing agent for gold or gold alloy to prevent corrosion by covering the pinholes developed on the gold or gold alloys.

In performing surface treatment for gold or gold alloys with the sealing agent of the present invention, as described above, the copper or copper alloy-made electronic components, which are generally subjected to the nickel plating as the base plating followed by gold or gold alloy plating on the nickel plating, are used as the processed material. The composition of the present invention is adjusted to 20 to 80° C., preferably 30 to 60° C. The processed material is brought into contact with the above composition for 0.1 seconds to 5 minutes, preferably for 1 second to 1 minute. Contact may be established by dipping, spraying, or other such methods. It is then preferably washed for 1 to 60 seconds with deionized water and dried.

The compositions of the present invention are suitable for the surface treatment agent for electronic equipment and electronic components having gold or gold alloy plating film on its surface; preferably, it can be used as the surface treatment agent for the gold or gold alloy plating film formed on the connection terminal surface of the electronic components. For example, the composition can be used as the surface treatment agent for the gold or gold alloy plating film formed on the surface of the electrode terminals of semiconductor elements, connectors to connect electronic equipment, and the like. For gold or gold alloy plating, a hard gold plating solution is usually used, for example, gold cobalt alloy plating, gold nickel alloy plating, and the like.

Hereinafter, the present invention will be explained with reference to the Examples; however, the present invention is not limited to these Examples.

EXAMPLE 1

The electronic components (copper alloy 194) of copper material subjected to nickel electroplating (coating thickness of 2 microns) followed by gold electroplating (coating thickness of 0.026 microns) were used as the test sample. The composition 1 of the following composition was adjusted to 45° C., and the test sample was immersed for 5 seconds, and the surface treatment was performed. The test sample was then rinsed with deionized water and dried with air knife and hot air.

Composition 1

Cationic polymer obtained from imidazole and epichlorohydrin (Product name: RALU® PLATE IME manufactured by Raschig Chemicals): 20 g/L
Sodium polyphosphate (manufactured by Taihei Chemical Industrial Co., Ltd.): 20 g/L
Remaining part: Water Corrosion Test
Neutral salt spray test (NSS test)
Conditions
Spray solution: 5% sodium chloride aqueous solution
Temperature: 34 to 36° C.
pH: 6.5 to 7.2
Spray amount: Horizontal collecting area 0.5 to 3.0 ml/h per 80 $cm^2$
Spray time: 48 hours or 72 hours
Spray angle: 20 degrees to the vertical line
Evaluation method: A state of corrosion developed on the surface of the test sample after an elapse of predetermined time was checked with the naked eye and rank was given according to the following criteria. Then, groove-like corrosion was counted with a microscope of 10 times.

Evaluation criteria
Level 0: No corrosion
Level 1: About 1 to 9% of the area of the test sample surface is corroded
Level 2: About 10 to 29% of the area of the test sample surface is corroded
Level 3: About 30 to 49% of the area of the test sample surface is corroded
Level 4: About 50% or more of the area of the test sample surface is corroded Examples 2-3, Comparative Examples 1 to 8

Operation was performed in the same manner as in Example 1 except the concentration of the composition was changed to the composition as described in Table 1 to 3, to assess the degree of corrosion. Results are shown in Table 1 to 3.

TABLE 1

| | | Example | | |
|---|---|---|---|---|
| Type | Compound Name | 1 | 2 | 3 |
| Cationic polymer | IME | 20 g/L | 20 g/L | 20 g/L |
| Phosphorous compound | Sodium polyphosphate | 20 g/L | — | — |
| | Sodium tripolyphosphate | — | 20 g/L | — |
| | Guanidine phosphate | — | — | 20 g/L |
| After 48 hours | Corrosion level | 0 | 0 | 0 |
| | Corrosion number | 0 | 0 | — |
| After 72 hours | Corrosion level | 0 | 0 | 1 |
| | Corrosion number | 5 | 4 | — |

TABLE 2

| | | Comparative Example | | | |
|---|---|---|---|---|---|
| Type | Compound Name | 1 | 2 | 3 | 4 |
| Cationic polymer | | — | — | — | — |
| Phosphorous compound | | — | — | — | — |
| Others | Benzotriazole | — | 1 g/L | — | — |
| | Mercaptosuccinic acid | — | — | 15 g/L | — |
| | Picolinic acid | — | — | — | 1 g/L |

TABLE 2-continued

| Type | Compound Name | Comparative Example | | | |
|---|---|---|---|---|---|
| | | 1 | 2 | 3 | 4 |
| After 48 hours | Corrosion level | 3 | 4 | 4 | 4 |
| | Corrosion number | 200 or above | 50 or above | 42 | 100 or above |
| After 72 hours | Corrosion level | 4 | — | — | — |
| | Corrosion number | 200 or above | — | — | — |

TABLE 3

| Type | Compound Name | Comparative Example | | | |
|---|---|---|---|---|---|
| | | 5 | 6 | 7 | 8 |
| Cationic polymer | IME | 20 g/L | 20 g/L | — | — |
| | H.C. polymer*[1] | — | — | 20 g/L | — |
| Phosphorous compound | Sodium polyphosphate | — | — | 20 g/L | 20 g/L |
| Others | Sorbitan monostearate (Solgen 40) | 1 g/L | — | — | — |
| | Polyethylene glycol (PEG 35000) | — | 1 g/L | — | — |
| | Polyoxyethylene sorbitan monostearate (Solgen TW 60) | — | — | — | 20 g/L |
| After 48 hours | Corrosion level | 4 | 4 | 4 | 3 |
| | Corrosion number | 100 or above | 100 or above | — | — |
| After 72 hours | Corrosion level | — | — | — | — |
| | Corrosion number | — | — | — | — |

*[1]Copolymer of N-pyrrolidone and N-dimethylaminoethyl methacrylate diethyl sulfonate, manufactured by Osaka Organic Chemical Co., Ltd.

What is claimed is:

1. A surface treatment method for gold or gold alloy comprising: a) providing a copper or copper alloy-made electronic component, b) nickel plating the copper or copper alloy-made electronic component, c) gold or gold alloy plating the nickel, and d) contacting a surface of the gold or the gold alloy with an aqueous solution consisting of a cationic polymer, wherein the cationic polymer comprises a reaction product of a nitrogen-containing heterocyclic compound and epihalohydrin, a phosphorus compound, water, and optionally a pH adjuster and a wetting agent, to seal pinholes in the gold or gold alloy.

2. The surface treatment method of claim 1, wherein the phosphorus compound is selected from the group consisting of phosphoric acids, polyphosphoric acids and salts thereof and phosphate esters.

3. The surface treatment method of claim 1, wherein the cationic polymer is in amounts of 0.01 to 70 g/L, and the phosphorus compound is in amounts of 0.01 to 50 g/L.

4. The surface treatment method of claim 3, wherein the cationic polymer is in amounts of 1 to 20 g/L.

5. The surface treatment method of claim 3, wherein the phosphorus compound is in amounts of 10 to 30 g/L.

6. The surface treatment method of claim 1, wherein a pH of the aqueous solution is from 6-12.

7. The surface treatment method of claim 6, wherein the pH of the aqueous solution is from 8-12.

8. The surface treatment method of claim 1, wherein the nitrogen-containing heterocyclic compound is chosen from imidazole or pyridine.

9. The surface treatment method of claim 1, wherein the epihalohydrin is chosen from epihalohydrin or epibromohydrin.

10. The surface treatment method of claim 1, wherein the surface treatment with the aqueous solution is done without performing electrolysis.

\* \* \* \* \*